United States Patent [19]

Elsheikh et al.

[11] Patent Number: 5,895,825
[45] Date of Patent: Apr. 20, 1999

[54] PREPARATION OF 1,1,1,3,3-PENTAFLUOROPROPANE

[75] Inventors: Maher Y. Elsheikh, Wayne; Michael S. Bolmer, Collegeville; Bin Chen, Exton, all of Pa.

[73] Assignee: Elf Atochem North America, Inc., Philadelphia, Pa.

[21] Appl. No.: 08/980,747

[22] Filed: Dec. 1, 1997

[51] Int. Cl.⁶ .................................................. C07C 17/08
[52] U.S. Cl. ........................ 570/167; 570/169; 570/164
[58] Field of Search ............................... 570/169, 167, 570/164

[56] References Cited

U.S. PATENT DOCUMENTS 5,616,819  4/1997  Boyce et al. ........................... 570/167

*Primary Examiner*—Alan Siegel

[57] ABSTRACT

A process for the preparation of 245fa is provided, wherein 1233zd is first fluorinated to 1234ze, followed by fluorination of 1234ze to 245fa. 245fa is a known foam blowing agent and refrigerant.

5 Claims, No Drawings

PREPARATION OF 1,1,1,3,3-PENTAFLUOROPROPANE

BACKGROUND OF THE INVENTION

This invention relates to the preparation of 1,1,1,3,3-pentafluoropropane ("245fa") from 1,1,1-trifluoro-3-chloro-2-propene ("1233zd"), particularly to processes wherein said 1233zd is first converted to 1,1,1,3-tetrafluoro-2-propene ("1234ze"), followed by conversion of the 1234ze to 245fa. 1,1,1,3,3-Pentafluoro-propane is known to have utility as a foam blowing agent and refrigerant.

U.S. Pat. No. 5,616,819 discloses the conversion of 1233zd to 245fa in one step via reaction with excess hydrogen fluoride, but separation of the resulting reaction mixture is tedious because 245fa forms azeotropes with the 1233zd and excess HF. Thus, the '819 patent teaches use of organic salts to aid in recovery of the 245fa, all three compounds having similar boiling points. What is desired is a manner of producing readily recoverable 245fa.

BRIEF SUMMARY OF THE INVENTION

A process for preparing readily recoverable 245fa is provided, which process comprises (a) contacting 1233zd with hydrogen fluoride (hereinafter for convenience referred to as "HF") in a first reaction zone under conditions sufficient to produce 1234ze and (b) contacting said 1234ze with HF in a second reaction zone under conditions sufficient to produce 245fa. Because 1234ze readily reacts with HF, it is not necessary to use large molar excesses of HF in step (b). The reaction mixture from step (a) contains primarily 1234ze, 245fa and hydrogen chloride ("HCl"), together with unreacted 1233zd and HF. The 245fa, 1233zd and HF can be separated from this mixture and recycled to the first reaction zone, such as by distillation to separate the reaction into streams containing (i) the 245fa, 1233zd and HF and (ii) 1234ze and HCl. The 1234ze and HCl in the second stream (ii) can be separated by methods known in the art, such as by a second distillation or by absorption wherein the HCl is removed, for example, by absorption in water or caustic solution.

DETAILED DESCRIPTION

A process has now been discovered for producing readily recoverable 245fa by converting 1233zd to 1234ze, followed by conversion of 1234ze to 245fa. The 1234ze intermediate has a boiling point 35° C. lower than that of 1233zd, so that it can be readily separated from 245fa via distillation. Further, 1234ze readily reacts with HF, so that large excesses of HF are not required in the second step, again simplifying recovery.

The 1233zd starting material can be prepared by known processes, such as fluorination of 1,1,3,3-tetrachloro-2-propene ("1230za") as taught in U.S. Pat. No. 5,616,819.

The first step of the process involves contacting 1233zd with HF in a first reaction zone under conditions sufficient to produce 1234ze, such as by the gas phase, catalyzed fluorination of 1233zd to produce a mixture whose major components are 1234ze, 245fa, HF, HCl and 1233zd. The HF: 1233zd molar ratio is typically from about 0.5:1 to 40:1, but is preferably at least about 1:1 to enhance conversion and no more than about 10:1 in order to produce lower levels of HF downstream to recover. Temperatures of from about 250° C. to about 600° C. are typically used, preferably from about 300° C. to about 500° C. Pressures are typically from about 0 to about 400 psig, preferably from about 20–200 psig. A variety of fluorination catalysts can be used, such as aluminum fluoride or a chromium-based catalyst (such as chromium oxide, $Cr_2O_3$), which chromium-based catalyst is either unsupported or supported on fluorided alumina or activated carbon, the chromium catalyst being used alone or in the presence of a co-catalyst such as an alkali metal (for example, sodium, potassium or lithium), alkaline earth metal (for example, calcium, barium or magnesium), zinc, manganese, cobalt or nickel. Two such preferred chromium catalysts are chromium oxide and chromium/nickel on fluorided alumina, preparation of this latter catalyst being taught, for example, in European Patent 486333. The chromium-based catalysts are preferably activated before use, typically by a procedure wherein the catalyst bed is heated to about 370°–380° C. (normally with a continuous flow of nitrogen), after which a mixture of approximately equal volumes of HF and air or nitrogen (preferably nitrogen) are fed over the catalyst bed for about 18 hours. An oxygen or chlorine cofeed can also be used to extend the catalyst lifetime, typically in an amount of from about 0.005 to about 0.20 moles of chlorine or oxygen per mole of organic in the feed, the oxygen being introduced as an oxygen-containing gas such as air, oxygen, or an oxygen/nitrogen mixture. Contact times (catalyst volume divided by the total flow rate of reactants and cofeeds at the operating temperature and pressure of the process) are typically from about 1 to about 250 seconds, more typically from about 1 to about 120 seconds.

The 1234ze produced in the first reaction zone is preferably separated from the reaction mixture and then contacted with HF in a second reaction zone under conditions sufficient to produce 245fa. One manner of carrying out the separation is to subject the reaction mixture from the first reaction zone to two distillations, the first distillation serving to separate the lower boiling 1234ze and HCl (taken off at top of the column) from the 245fa, 1233zd, HF and any other heavies (taken off at the bottom of the column), with the second distillation serving to separate the lower boiling HCl (removed at top of column) from the 1234ze (removed at column bottom and fed to second reaction zone). Preferably, the bottoms from the first column are then recycled to the first reaction zone, where the 1233zd and 245fa can be reacted to produce 1234ze. The fluorination of 1234ze to 245fa in the second reaction zone can be carried out using a catalyzed gas phase, liquid phase, or mixed phase system to produce a mixture whose major components are 245fa, 1234ze and HF. Since 1234ze reacts readily with HF, the HF: 1234ze molar ratio is typically from about 0.1:1 to about 3:1, preferably from about 1:1 to about 1.5:1 so as to avoid a concentration of HF in the product stream in excess of the HF/245fa azeotrope. Temperatures of from about 30° C. to about 300° C. are typically used, preferably from about 50° C. to about 200° C. Pressures are typically from about 0 to about 300 psig, preferably from about 30–200 psig. A variety of fluorination catalysts can be used, such as supported Lewis acids, including the oxides or salts (preferably chlorides) of Sb(V), Ti(IV), Sn(IV), Ta(V) or Nb(V) on activated carbon, the chromium-based catalysts discussed above or sulfonic acid containing compounds such as trifluoromethanesulfonic acid supported on activated carbon or activated alumina. If the process is run as a gas phase reaction at a low temperature (up to about 130° C.), the supported Lewis acid or sulfonic acid catalysts are preferred. If the gas phase process is carried out a higher temperature, then the chromium-based catalysts are preferred. If the process is run as a liquid phase reaction, the supported Lewis acid or sulfonic acid catalysts are preferred. Each type of catalyst will have its own activation procedure prior to use. Activation for the chromium-based catalysts is as discussed above. The supported Lewis acids and sulfonic acids have a lower activation temperature, typically about 50° C., using a slow feed of HF diluted with nitrogen to convert the metal chloride into metal fluoride. Contact times for the gas phase reaction (catalyst volume divided by the total flow rate of reactants and cofeeds) are typically from about 1 to about 250 seconds, more typically from about 1 to about 120 seconds, while residence time for the liquid phase reaction is typically from about 1 to about 400 minutes, more typically from about 10 to about 120 minutes. The 245fa (boiling point 15° C.) can then be recovered from the reaction mixture by conventional techniques, such as distillation, the lower boiling 1234ze (boiling point −16° C.) and any HF/245fa azeotrope coming off overhead, where it can be recycled to the reactor. Separation of any HF/245fa azeotrope can be conducted as taught, for example, in world patent application WO97/27163.

The practice of the invention is illustrated in more detail in the following non-limiting examples.

EXAMPLE 1
Fluorination of 1233zd to 1234ze with (unsupported) chromium oxide catalyst Chromium oxide catalyst ($Cr_2O_3$) was activated at 380° C. by cofeeding a mixture of HF (124 cc/min) and air (100 cc/min) for 18 hours. 1233zd and HF, in a molar ratio of HF: 1233zd of 10.6: 1, were then fed to the reactor at 365° C. and 38 psig for a contact time of 3.9 seconds, resulting in 54.8% conversion of the 1233zd, with selectivity being 58.3% for 1234ze and 36.6% for 245fa. In subsequent runs at a molar ratio of HF: 1233zd of 21.1:1 while holding other parameters the same, essentially the same results were obtained. Still further tests indicated that higher pressure (154 psig) and longer contact time (14 seconds) increased conversion to about 74%, while lower pressure (28 psig) and shorter contact time (3.5 seconds) improved selectivity for 1234ze to about 61%.

EXAMPLE 2
Fluorination of 1233zd to 1234ze using supported chromium/nickel catalyst The catalyst for this example was a mixture of chromium and nickel oxides supported on fluorided alumina (prepared as in European Patent 486333), which catalyst was activated at 380° C. by cofeeding a mixture of HF (123 cc/min) and nitrogen (100 cc/min) for 18 hours. 1233zd and HF, in varying molar ratios ("m.r."s), were then fed, together with a cofeed of air containing 0.03 moles of oxygen per mole of organic (1233zd), over the activated catalyst under the conditions, and with the results, set forth below:

| Run # | 1 | 2 | 3 | 4 | 5 | 6 |
|---|---|---|---|---|---|---|
| Temperature (° C.) | 300 | 354 | 354 | 353 | 354 | 404 |
| Pressure (psig) | 150 | 157 | 156 | 43 | 43 | 153 |
| HF:1233zd (m.r.) | 2.9 | 2.6 | 5.3 | 2.6 | 5.2 | 2.6 |
| Contact time (seconds) | 18.5 | 9.4 | 9.5 | 4.8 | 4.7 | 17.1 |
| Conversion (%) | 43.1 | 37.3 | 51.0 | 30.5 | 42.6 | 30.8 |
| Selectivity for 1234ze (%) | 13.2 | 28.1 | 24.1 | 45.0 | 43.2 | 35.9 |
| Selectivity for 245fa (%) | 86.9 | 71.8 | 75.8 | 54.9 | 56.7 | 64.0 |

EXAMPLE 3
Gas Phase Fluorination of 1234ze to 245fa with (unsupported) chromium oxide catalyst Using the same catalyst and activation procedures as in EXAMPLE 1, 1234ze and HF, in a mole ratio of HF: 1234ze of 1.6: 1, were fed to a reactor at a temperature of 204° C. and 151 psig for a contact time of 77 seconds, resulting in 98.9% conversion of the 1234ze to 245fa and 79.8% conversion of the HF.

EXAMPLE 4
Gas Phase Fluorination of 1234ze to 245fa using antimony chloride catalyst supported on activated carbon ($SbCl_5/C$)

38 Grams of $SbCl_5/C$ catalyst was activated at 50° C. by cofeeding a mixture of HF (123 cc/min.) and nitrogen (100 cc/min.) for 18 hours. HF and 1234ze, in a molar ratio of 1.04: 1, were then fed to the reactor under the conditions, and with the results, set forth below:

| Run # | 1 | 2 | 3 | 4 |
|---|---|---|---|---|
| Temperature (° C.) | 123 | 128 | 119 | 115 |
| Pressure (psig) | 147 | 147 | 147 | 148 |
| Contact time (seconds) | 50.7 | 49.9 | 51.1 | 51.8 |
| Conversion of 1234ze (%) | 99.7 | 97.6 | 95.3 | 95.1 |
| Selectivity for 245fa (%) | 100 | 100 | 100 | 100 |

We claim:

1. A process for preparing 1,1,1,3,3-pentafluoropropane which comprises (a) contacting 1,1,1 -trifluoro-3-chloro-2-propene with hydrogen fluoride in a first reaction zone under conditions sufficient to produce a reaction mixture containing 1,1,1,3-tetrafluoro-2-propene; and (b) seperating the 1,1,1,3-tetrafluoro-2-propene from said reaction mixture and contacting it with hydrogen fluoride in a second reaction zone under conditions sufficient to produce 1,1,1,3,3-pentafluoropropane.

2. A process as in claim 1 wherein the molar ratio of hydrogen fluoride to 1,1,1,3-tetrafluoro-2-propene in step (b) is at most about 3 to 1.

3. A process for preparing 1,1,1,3,3-pentafluoropropane which comprises (a) contacting 1,1, 1-trifluoro-3-chloro-2-propene with hydrogen fluoride in a first reaction zone under conditions sufficient to produce a reaction mixture containing 1,1,1,3-tetrafluoro-2-propene, 1,1,1,3,3-pentafluoropropane, and hydrogen chloride, together with unreacted 1,1,1-trifluoro-3-chloro-2-propene and hydrogen fluoride; and (b) separating the 1,1,1,3-tetrafluoro-2-propene from said reaction mixture and contacting it with hydrogen fluoride in a second reaction zone under conditions sufficient to produce 1,1,1,3,3-pentafluoropropane.

4. A process as in claim 3 wherein the 1,1,1,3,3-pentafluoropropane, 1,1,1-trifluoro-3-chloro-2-propene and hydrogen fluoride are separated from the reaction mixture in step (a) and recycled to the first reaction zone.

5. A process as in claim 3 wherein the reaction mixture from step (a) is subjected to a first distillation to separate the reaction mixture into a first stream containing the 1,1,1,3, 3-pentafluoropropane, 1,1,1-trifluoro-3-chloro-2-propene and hydrogen fluoride and a second stream containing the 1,1,1,3-tetrafluoro-2-propene and hydrogen chloride, the hydrogen chloride in the second stream then being separated from the 1234ze via absorption or a second distillation.

* * * * *